United States Patent [19]

Buss

[11] 4,049,703

[45] Sept. 20, 1977

[54] PROCESS FOR THE PRODUCTION OF PURIFIED CAMPHORSULFONIC ACID SALTS

[75] Inventor: David R. Buss, Portage, Mich.

[73] Assignee: The Upjohn Company, Kalamazoo, Mich.

[21] Appl. No.: 851,084

[22] Filed: Aug. 18, 1969

[51] Int. Cl.$^2$ ............................................ C07C 143/00
[52] U.S. Cl. ..................................................... 260/503
[58] Field of Search .............................. 260/503, 505 P

[56] References Cited

U.S. PATENT DOCUMENTS 3,221,046  11/1965  Johnson et al. ....................... 260/503

OTHER PUBLICATIONS

Groggins, "Unit Processes in Organic Synthesis", pp. 540, 541, 549, (1935).

Primary Examiner—Bernard Helfin
Assistant Examiner—A. Siegel
Attorney, Agent, or Firm—Martin B. Barancik; Sidney B. Williams

[57] ABSTRACT

A liquid ion exchange process for recovering a concentrated purified aqueous solution of a camphorsulfonic acid salt from a dilute impure solution of the same wherein the ion exchange medium is a liquid secondary amine and the pH of the mixture during the ion exchange is maintained at 3 - 6 by treating the mixture with a polyprotic acid having two pKs of less than 2.5.

7 Claims, No Drawings

PROCESS FOR THE PRODUCTION OF PURIFIED CAMPHORSULFONIC ACID SALTS

BRIEF SUMMARY OF THE INVENTION

This invention relates to a liquid ion exchange method for recovering a concentrated purified aqueous solution of a camphorsulfonic acid salt which comprises (a) mixing a dilute impure solution of said salt with a solution of a liquid secondary amine and a water-immiscible solvent while maintaining the pH of the mixture of 3 – 6 by the addition of a polyprotic acid having two pKs of less than 2.5, (b) separating the organic phase from the mixture, (c) mixing the organic phase with a smaller volume of water at a pH about 9 to form a second two-phase mixture and (d) separating the aqueous phase from said two-phase mixture to provide a purified concentrated aqueous solution of said salt.

BACKGROUND OF THE INVENTION

This invention relates to an improved process for the recovery of camphorsulfonic acids and more particularly, to an improved process for the purification and concentration of aqueous solutions of soluble salts of 10-d-camphorsulfonic acid.

Resolutions of racemic bases are carried out by means of the use of optically active acids. For example, 10-d-camphorsulfonic acid is an extremely effective resolving agent but it is costly. It must, therefore, be recovered efficiently and in a purified form to make a process economical.

An example of the use of 10-d-camphorsulfonic acid as a resolving agent is the resolution of DL-phenylglycine to D-phenylglycine, a material of importance in making semisynthetic penicillins. During the process a relatively dilute aqueous solution of 10-d-camphorsulfonic acid, as its sodium salt, is recovered along with other undesirable inorganic salts. The resolving agent needs to be concentrated and at the same time the inorganic salts removed selectively.

A liquid ion exchange method for recovering a concentrated purified aqueous solution of 10-d-camphorsulfonic acid is disclosed in U.S. Pat. No. 3,221,046. However, in order to obtain reasonable recoveries utilizing the patentees process it is necessary to utilize a multi-stage counter-current operation (3-5 theoretical stages). Another problem in this process is the instability of the system due to large volume changes in phases from stage to stage.

Theoretically, the problem can be explained in terms of competition for the exchange sites in the liquid ion exchanger. For example, if the only other anion in the aqueous phase were chloride (for example, from hydrochloric acid used to regenerate the 10-d-camphorsulfonic acid as was the case in the process described in U.S. Pat. No. 3,221,046) an equilibrium condition exists:

$$LA\text{-}1\cdot HCl + CSA^- \rightleftarrows La\text{-}1\cdot HCSA + Cl^-$$

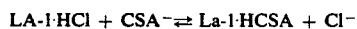

wherein LA-1 is a liquid secondary amine or mixture thereof, $CSA^-$ is the anion of 10-d-camphorsulfonic acid, HCSA is 10-d-camphorsulfonic acid, and where the free ions are in the aqueous phase and acids are bound to the secondary amine, LA-1, in the organic phase. Assuming that this is truly the form of the equilibrium, an average value for the equilibrium constant was found from our experiments as follows:

$$K^{CSA-}_{Cl-} = \frac{[CSA^-]_o[Cl^-]_A}{[CSA^-]_A[Cl^-]_o} = 16.7$$

where the subscripts A and o mean aqueous and organic phases respectively. The total number of sites in the organic phase is determined by the amount of acid present in the system until all the sites (capacity) are exhausted. Using the quantities normally used during the process, one can calculate that a single stage recovery process with hydrochloric acid recovers only about 72% of the camphorsulfonic acid.

The present invention resides in the use of a polyprotic acid, such as sulfuric acid, rather than a monoprotic acid, such as hydrochloric acid, to maintain the pH of the ion exchange system at a pH of 3 – 6. The selectivity of the liquid ion exchange process for a monoprotic anion over the diprotic sulfate is surprising since the opposite affect usually occurs when solid ion exchangers are used.

The equilibrium is written:

$$(LA\text{-}1\cdot H)_2SO_4 + 2CSA^- \rightleftarrows 2LA\text{-}1\cdot HCSA + SO_4^=$$

Assuming that this is truly the form of the equilibrium, an average value for the equilibrium constant was found from our experiments as follows:

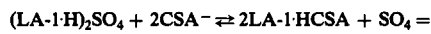

$$K^{CSA-}_{SO_4^=} = \frac{[CSA^-]^2_o[SO_4^=]_A}{[CSA^-]^2_A[SO_4^=]_o} = 1.3 \times 10^4$$

which gives a 92 – 98% recovery of 10-d-camphorsulfonic acid in the form of its sodium salt for a single stage recovery process. In order to have sulfate as the only anion competing with the camphorsulfonate, sulfuric acid would be used to regenerate the camphorsulfonic acid for the resolution process as well as being used in the recovery process.

Mixed polyprotic acids could be used in this process still giving a high selectivity for and high yield of the camphorsulfonic acid salt.

DETAILED DESCRIPTION

The starting solution of the process can be a dilute aqueous solution of a salt of a camphorsulfonic acid, for example it can be an aqueous solution of sodium d-10 camphorsulfonic acid that is recovered from the resolution of a racemic mixture of DL-phenylglycine.

This solution is first mixed at a pH of 3 – 6 with a solution of a water-immiscible organic solvent and a secondary amine having the formula

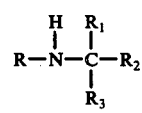

wherein R is an aliphatic group having from 10 to 14 carbon atoms and R, $R_2$ and $R_3$ are each alkyl and wherein the combined carbon atoms in $R_1$, $R_2$ and $R_3$ total from 11 to 14 to form a two-phase mixture.

A preferred group of amines are a group of amines having the formulae (A)

-continued

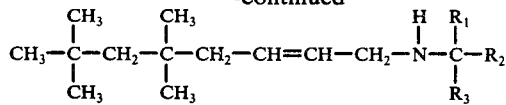

and

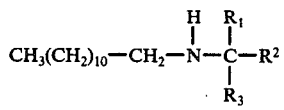 (B)

wherein $R_1$, $R_2$ and $R_3$ are the same as above. The mixture of amines illustrated by formulas A and B are commonly referred to as "Liquid Amine Mixture No. I (LA-1)" and "Liquid Amine Mixture NO. II (LA-2)" respectively. The characteristics of both of these mixtures are described in U.S. Pat. No. 3,221,046 and they are both readily available.

The pH of the mixture is maintained by adding a polyprotic acid having two pKs of less than 2.5. The preferred acid is sulfuric acid, however, other polyprotic acids such as the phosphoric acids can be used. After thorough mixing the phases are allowed to separate.

The organic phase is then separated from the mixture and treated with distilled water.

The resulting mixture is vigorously stirred and treated with sodium hydroxide until a pH of 9 is reached and then the stirring is stopped to allow the phases to separate. Other bases capable of forming water soluble salts with 10-d-camphorsulfonic acid, i.e., potassium hydroxide, ammonium hydroxide, may be used instead of sodium hydroxide to control the pH in this step.

The aqueous phase which contains the sodium salt of 10-d-camphorsulfonic acid and small traces of the organic phase, colored organic impurities and sodium sulfate is separated from the mixture. Relatively pure sodium 10-d-camphorsulfonate is recovered from the aqueous phase by filtration through an activated carbon bed to remove unwanted organic materials and then evaporation to dryness.

The following example is set forth to illustrate the invention and to enable persons skilled in the art to better understand and practice the invention and is not intended to limit the same.

EXAMPLE

About 1500 ml. of mother liquor containing 0.65 moles of sodium 10-d-camphorsulfonate and 1.0 moles sodium sulfate and a solution containing 400 ml. of LA-1 and 1000 ml. toluene are mixed. About 20 ml. of sulfuric acid are added while vigorously stirring the mixture until a pH of 3.5 is reached. After addition of the acid, the organic phase which now contains most of the 10-d-camphorsulfonic acid is separated and mixed with 260 ml. of distilled water. The resulting mixture is vigorously stirred and treated with 50% sodium hydroxide until a pH of greater than 9 is reached. After the addition of the sodium hydroxide is completed, stirring is discontinued to allow the phases to separate. The aqueous phase which now contains the sodium 10-d-camphorsulfonate is separated and worked up while the LA-1 solution is saved for another recovery cycle.

In addition to the sodium 10-d-camphorsulfonate, the aqueous phase also contains sodium sulfate and traces of organic materials such as toluene and LA-1. These organic materials are removed by filtering the aqueous solution through a filter cake containing about 5 gm. of Darco G-60, an activated carbon, and 5 gm. of a filter aid. Washing the filter cake with about 20 ml. of distilled water yields about 450 ml. of a purified aqueous solution of sodium 10-d-camphorsulfonate containing about 0.62 moles of the sodium 10-d-camphorsulfonate (95% recovery) and about 0.05 moles sodium sulfate. Concentration to dryness yields about 172 gm. of solids.

Other camphorsulfonic acids that can be recovered by this process include 10-l-camphorsulfonic acid, 10-dl-camphorsulfonic acid, 3-d-camphorsulfonic acid, 3-l-camphorsulfonic acid, 3-dl-camphorsulfonic acid, 9-d-camphorsulfonic acid, 9-l-camphorsulfonic acid, 9-dl-camphorsulfonic acid, 8-d-camphorsulfonic acid, and 8-dl-camphorsulfonic acid.

I claim:

1. In a process of purifying an aqueous solution of a camphorsulfonic acid salt which comprises (a) mixing at a pH of 3-6 a dilute aqueous solution of the camphorsulfonic acid salt and a solution consisting of a water-immiscible organic solvent and a secondary amine that is liquid at room temperature, soluble in the organic water-immiscible solvent, and is

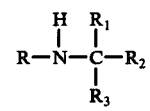

wherein R is an aliphatic group having from 10 to 14 carbon atoms and $R_1$, $R_2$ and $R_3$ are each alkyl and wherein the combined carbon atoms in $R_1$, $R_2$ and $R_3$ total from 11 to 14, (b) separating the organic water-immiscible phase from the mixture, (c) mixing the organic water-immiscible phase with a volume of water that is less than half the original aqueous solution volume at a pH above 9 to form a second two-phase mixture, and (d) separating the aqueous phase from said two-phase mixture to provide a purified concentrated aqueous solution of the salt; the improvement consisting of sulfuric acid to control the pH of the mixture formed in Step (a).

2. In a process of recovering a purified aqueous solution of a camphorsulfonic acid salt from an impure dilute aqueous solution of said salt, said impurities comprising inorganic salts, which comprises (a) mixing at a pH of 3-6 an impure dilute aqueous solution of the camphorsulfonic acid salt and a solution consisting of a water-immiscible organic solvent and a secondary amine that is liquid at room temperature, soluble in the organic water-immiscible solvent, and is

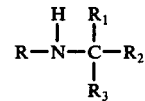

wherein R is an aliphatic group having from 10 to 14 carbon atoms and $R_1$, $R_2$ and $R_3$ are each alkyl and wherein the combined carbon atoms in $R_1$, $R_2$ and $R_3$ total from 11 to 14, (b) separating the organic water-immiscible phase from the mixture, (c) mixing the organic water-immiscible phase with a volume of water that is less than half the original aqueous solution volume at a pH above 9 to form a second two-phase mixture, and (d) separating the aqueous phase from said two-phase mixture to provide a purified concentrated aqueous solution of the salt; the improvement consisting of utilizing sulfuric acid to control the pH of the mixture formed in Step (a).

3. A process in accordance with claim 2 wherein the secondary amine is selected from the group consisting of

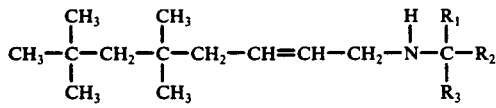

and

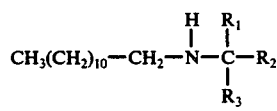

wherein $R_1$, $R_2$ and $R_3$ are each alkyl and wherein the combined carbon atoms in $R_1$, $R_2$ and $R_2$ total from 11 to 14.

4. A process in accordance with claim 3 wherein the amine is selected from the group consisting of

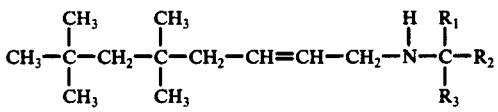

wherein $R_1$, $R_2$ and $R_3$ are each alkyl and wherein the combined carbon atoms in $R_1$, $R_2$ and $R_3$ total from 11 to 14.

5. A process in accordance with claim 4 wherein the water-immiscible organic solvent is toluene.

6. A process in accordance with claim 5 wherein the camphorsulfonic acid salt is sodium 10-d-camphorsulfonate.

7. A process in accordance with claim 6 wherein the mixing of the aqueous solution of dilute impure camphorsulfonic acid with a solution consisting of toluene and a secondary amine is done in one stage.

* * * * *